United States Patent [19]

Bassingthwaighte et al.

[11] Patent Number: 4,606,908

[45] Date of Patent: Aug. 19, 1986

[54] METHODS AND COMPOSITIONS FOR PLASMA AND ORGAN IMAGING

[75] Inventors: James B. Bassingthwaighte; Stephen E. Little; Kenneth A. Krohn, all of Seattle, Wash.

[73] Assignee: Washington Research Foundation, Seattle, Wash.

[21] Appl. No.: 538,852

[22] Filed: Oct. 4, 1983

[51] Int. Cl.$^4$ ..................... A61K 43/00; A61K 49/00
[52] U.S. Cl. .................................... 424/1.1; 540/590; 424/9
[58] Field of Search ............. 424/1.1, 9; 260/239 BB, 260/239 D

[56] References Cited

U.S. PATENT DOCUMENTS 4,124,583  11/1978  Georgiev et al. ............... 260/239 D
4,495,281  1/1985   Buckler et al. .................. 435/7

FOREIGN PATENT DOCUMENTS 55294  12/1959  Australia ..................... 260/239 D

OTHER PUBLICATIONS

Lee et al., Synthesis and Applications of Isotopically Labeled Compounds, Proceedings of an International Symposium, Kansas City, MO, U.S.A., 6-11 Jun. 1982, W. P. Duncan et al, eds., 203-204.

Preskoen et al., J. Pharmacol. Exp. Therapeut., 213 (2) 313-20, (1980).

Fed. Proc. (1983) 42: "Intraorgan Regional Plasma Flows Using Highly Extracted Solute Desmethylimipramine", Little et al.

*Primary Examiner*—Christine M. Nucker
*Attorney, Agent, or Firm*—Townsend & Townsend

[57] ABSTRACT

Halogenated dibenzazepines, particularly flouro- or iododesmethylimipramine, find use for measuring regional blood flows and for retention in particular organs for radioactive imaging. Such compositions are introduced into the arterial flow leading to the organ, and the compositions bind to the organ as a result of interaction with cellular receptors. The compositions have been found to display very high retention rates in the organ for relatively long periods of time.

9 Claims, No Drawings

METHODS AND COMPOSITIONS FOR PLASMA AND ORGAN IMAGING

BACKGROUND OF THE INVENTION

1. Field of the Invention

In both research and medical diagnosis, there is a frequent need for the ability to determine regional plasma flows, as well as to image flow to specific organs. These two needs share certain requirements for markers capable of fulfilling these functions. The material should be removed from plasma during a single transorgan passage; should be well retained by virtue of a large volume of distribution or large number of receptor sites; and should provide for detectable radioemission.

There is a continuing need for compounds which can serve as indicators of blood flow and provide for imaging of specific organs.

2. Description of the Prior Art

Prior methods of regional blood flow used ceramic or plastic microspheres (which dwell permanently in the tissue and are not suitable for human study) or albumin microspheres (which are not satisfactory) or molecules such as antipyrine or thallium which are either not well retained or are poorly extracted.

Little and Bassingthwaighte, Intraorgan Regional Plasma Flows Using Highly Extracted Solute Desmethylimipramine. Fed. Proc. 42:580, 1983 (Abstract) reported the use of tritiated desmethylimipramine as a soluble indicator for regional plasma flow. A chlorinated imipramine has been reported in the literature. Tritiated desmethylimipramine is available from New England Nuclear No. NET593.

SUMMARY OF THE INVENTION

Halogenated tricyclic antidepressants ("dibenzazepines"), particularly iodo- or fluoro-substituted desmethylimipramine, are employed as a plasma soluble nonparticulate marker for the determination of hemodynamic parameters, e.g., intraorgan regional flows and for clinical scintigraphic evaluation, by employing radioactive iodine as the radionuclide. The marker may be readily introduced into the blood stream and is retained by cellular receptors for desmethylimipramine.

DESCRIPTION OF THE SPECIFIC EMBODIMENTS

Radioactive halogen substituted tricyclic antidepressants are employed for measuring hemodynamic parameters, e.g., plasma intraorgan regional flows, and for use in clinical organ imaging, e.g., scintigraphic evaluation, tomography, etc., of specific organs. Particularly, the tricyclic antidepressant is halogenated, more particularly iodinated, to provided a halogenated product, which retains its binding capability to specific cellular receptors. More particularly, desmethylimipramine (10,11-dihydro-5-[3'-(methylamino)propyl]-5H-dibenz[b,f]azepine ("DMI") is halogenated to provide for mono- or di-halogenation, preferably monohalogenation.

The halogens are fluorine, chlorine, bromine and iodine, particularly fluorine, bromine and iodine, more particularly iodine. The iodine radionuclides include I-122, -123, -125, and -131 while the bromine radionuclides include Br-75, -76, -77, -78 and -82, and the fluorine radionuclides include F-18.

The radionuclide will be an emitter of detectable radiation which at the level of administration will not be harmful to the host. Generally, the radionuclide will have a relatively short half-life, ranging from about 3 min. to 60 days, usually about 60 min. to 7 days. The radiation may be gamma-radiation, positron or other high energy particle which can be detected by available equipment.

Any convenient technique for providing the halogenated product may be employed. Conveniently, the compound may be halogenated, particularly iodinated, employing electrophilic aromatic thallation. The process involves derivatization using $Th(OCOCF_3)_3$ followed by addition of the radiohalogen as an anion. The molar ratio of the Th to the dibenzazepine will be less than 1, generally in the range of 0.01 to 0.5. Excess non-radioactive iodide may be employed to completely remove Th from the dibenzazepine in order to facilitate purification and to increase radiochemical yield. Usually, the radionuclide will be present in a tracer, usually less than about 0.001 mole ratio based on the dibenzazepine. Depending upon the halogen used and amount of dibenzazepine used, the conditions will be varied, generally employing mild conditions, conveniently room temperature. Alternatively, a Sandmeyer reaction may be employed, involving nitration, reduction to amino, diazotization, and displacement with the radionuclide. The triazine displacement reaction is also useful for halogen (Wallach reaction). The manner of halogenation is not critical, so long as a physiologically acceptable product is obtained.

Where desmethylimipramine (DMI) is iodinated, employing thallium trifluoroacetate, the molar ratio of thallium to DMI will be from about 0.05 to 0.3, while the molar ratio of total iodide to DMI will vary from about 0.5 to 1.5. The temperature for the reaction will be in the range of about 10° to 30° C., conveniently ambient temperature, and the time for the reaction will be from about 5 min. to 2 hrs., usually 10 min. to 30 min. A variety of solvents may be employed, particularly trifluoroacetic acid. The concentration of DMI, may vary widely, generally being from about 0.05 to 1M. The product can be readily purified by precipitating the thallium with excess iodide and using high performance liquid chromatography employing as the solvent medium ethanolic aqueous phosphate buffer, pH 2–2.5, about 1–5 mM phosphate.

The product of particular interest is monohalogenated desmethylimipramine, where the halogen, particularly fluorine or iodine, atom is para to the ethylene bridge between the two benzene rings. This compound will be referred to as 3"-F or -I-DMI.

In order to demonstrate the use of $3''\text{-}^{125}I$-DMI as a marker for intraorgan regional flows, experiments were performed in isolated rabbit hearts to determine the extraction and retention of the compound. For isolated heart studies, after anesthesia with pentobarbital, the hearts were removed from 2 to 3 kg New Zealand white rabbits and mounted on a perfusion system in which the flow was controlled and the perfusion pressure monitored. The perfusate was (mM): Na 142, K 5.4, Mg 1.0, Ca 2.0, Cl 141, $HCO_3$ 12, $PO_4$ 0.435, glucose 11.0, and insulin 2 units/L, at 37° C. The coronary sinus flow and Thebesian flow into the right ventricle were collected via cannula placed through the pulmonary artery and a total effluent flow measured with graduated cylinder and stopwatch. Reference and test tracers were simultaneously injected as a mixed bolus into the aortic cannula, which supplied only the coronary system. Samples of the coronary sinus effluent were taken from the cannulated pulmonary artery at intervals of 1, 2, 4 or 10 seconds; higher sampling rates were used during the first part of the curves. The outflow of response was calculated as the fraction of dose emerging per unit time, h(t), at each time t:

$$h(t) = F \times C(t)/q_0$$

wherein:

F is the perfusate flow $ml \times s^{-1}$;

C(t) is the concentration of tracer, cpm/ml; and $q_0$ is the injected dose of tracer, cpm.

The residue function R(t) is defined:

$$R(t) = 1 - \int_0^t h(\lambda) d\lambda$$

$^{125}$I-DMI showed maximal instantaneous extractions of 96% at plasma flows up to 1.5 ml/min×g. Overall retentions of $^{125}$I-DMI at 1 min were about 91%, with retentions at 10-20 min of about 80%. There is the possibility, that the indicator compound employed was impure and, therefore, the result reported is minimum for early retention. These data clearly establish the subject compound as useful for an accurate measure of regional plasma flow.

The indicator will be usually introduced interarterially into a major artery providing blood to the organ of interest. Organs of interest include the heart, brain, liver, CNS, or other organ of interest. Depending on the purpose, the organ, radionuclide, and the like, the amount of marker injected may vary from about 0.1 μCi to 1 mCi. For intraorgan regional flow determinations, the amount will generally be from about 2 to 25 μCi, while for imaging, the amount will be from about 50 μCi to 1 mCi, more usually from about 100-500 μCi. The indicator will generally vary from about 0.1 to 100 Ci/mmole.

The indicator may be administered in any convenient physiological medium, such as saline, phosphate-buffered saline, saline having physiological amounts of other metals, e.g., K, Ca, Mg, glucose, insulin, or the like, in physiologically acceptable amounts. Generally, the concentration of the indicator will be dependent upon the radioactivity of the radionuclide atom and the intended dosage, but will be below pharmacologically significant levels.

Because of the high retention of the subject compounds for long periods of time in an organ, the radioactively labeled subject compounds can also be used for imaging. Because of the binding specificity of the subject compounds, those cells which specifically bind catechols, such as norepinephrine would preferentially adsorb the subject indicator, allowing for sharp contrast of organs having such receptors, as compared to other parts of the body.

The following examples are offered by way of illustration and not by way of limitation.

EXPERIMENTAL

Iodinated desmethylimipramine was prepared by combining 4.25 mg DMI and 5 μl of 0.8M thallium trifluoroacetate in 0.3 ml of trifluoroacetic acid at room temperature. After 15 min., 1mCi (5 μl) of $Na^{125}I$ (~6 Ci/mg) in 0.1N aq. NaOH was added; after 2 min., 10 μl of 0.8M KI in 0.1N aq. NaOH was added; after 5 min., 20 μl of sodium thiosulfate was added. The volatiles were evaporated with an air stream followed by purification on HPLC using C18 reverse phase column employing as the solvent, ethanolic aq. phosphate, 0.0125M, pH 2.3 in a volume ratio of 7:3.

In accordance with the subject invention, novel indicators are provided which allow for accurate measurements of intraorgan regional flows, as well as imaging of organs in vivo. The high lipid solubility, rapid uptake and high degree of retention make the subject compounds extremely useful as indicators.

Although the foregoing invention has been described in some detail by way of illustration and example for purposes of clarity of understanding, it will be obvious that certain changes and modifications may be practiced within the scope of the appended claims.

What is claimed is:

1. A method for concentrating a radioactive label in a functioning mammalian organ, which comprises: introducing into the arterial flow of said organ a fluid containing a radioactive halogenated desmethylimipramine in an amount sufficient for said radioactive dibenzazepine to become bound to said organ.

2. A method according to claim 1, wherein said radioactive halogenated desmethylimipramine is fluorinated or iodinated desmethylimipramine.

3. A method for imaging a target organ which comprises injecting into the arterial stream of a mammalian host upstream from said organ, a sufficient amount of radioactive fluorine or iodine substituted desmethylimipramine in a physiologically acceptable carrier, whereby said desmethylimipramine becomes concentrated in said target organ; and detecting the emissions from said radioactive fluorine or iodine bound to said target organ.

4. 3″-Halodesmethylimipramine, wherein said halo is radioactive fluorine or iodine.

5. 3″-Halodesmethylimipramine according to claim 4, wherein said iodine is $^{122}I$, $^{123}I$, $^{125}I$, or $^{131}I$.

6. 3″-Halodesmethylimipramine according to claim 4, wherein said fluorine is $^{18}F$.

7. A composition useful for imaging an organ in a mammalian host which comprises radioactive 3″-fluoro- or -iododesmethylimipramine in a physiologically acceptable carrier.

8. A composition according to claim 7, wherein said iodo is $^{122}I$, $^{123}I$, $^{125}I$, or $^{131}I$.

9. A composition according to claim 7, wherein said fluoro is $^{18}F$.

* * * * *

UNITED STATES PATENT AND TRADEMARK OFFICE
Certificate

Patent No. 4,606,908                                    Patented August 19, 1986

On petition requesting issuance of a certificate for correction of inventorship pursuant to 35 USC 256, it has been found that the above-identified patent, through error and without any deceptive intent, improperly sets forth the inventorship. Accordingly, it is hereby certified that the correct inventorship of this patent is James B. Bassingthwaighte, Stephen E. Little, Kenneth A. Krohn and Jeanne M. Link.

Signed and Sealed this 17th Day of February, 1987.

BRADLEY R. GARRIS,
*Office of the Deputy Assistant Commissioner for Patents.*